United States Patent
Probasco (10) Patent No.: US 7,767,234 B2
(45) Date of Patent: Aug. 3, 2010

(54) COMPOSITIONS AND METHODS FOR CONTROLLING A HONEY BEE PARASITIC MITE

(75) Inventor: Gene Probasco, Yakima, WA (US)

(73) Assignee: John I. Haas, Inc., Washington, DC (US)

( * ) Notice: Subject to any disclaimer, the term of this patent is extended or adjusted under 35 U.S.C. 154(b) by 250 days.

(21) Appl. No.: 11/396,360

(22) Filed: Mar. 31, 2006

(65) Prior Publication Data

US 2007/0232188 A1 Oct. 4, 2007

(51) Int. Cl.
*A01N 65/00* (2009.01)
*A61K 34/64* (2006.01)
*A61K 36/00* (2006.01)
*A01N 25/00* (2006.01)

(52) U.S. Cl. .................. 424/750; 424/539; 424/769; 424/405

(58) Field of Classification Search .............. None
See application file for complete search history.

(56) References Cited

U.S. PATENT DOCUMENTS

| | | | |
|---|---|---|---|
| 3,615,660 A | 10/1971 | Bavisotto et al. | |
| 4,148,873 A | 4/1979 | Owades | |
| 4,170,638 A | 10/1979 | Owades | |
| 4,867,731 A * | 9/1989 | Willard et al. | 449/2 |
| 5,227,162 A * | 7/1993 | Ferrari | 424/754 |
| 5,372,817 A | 12/1994 | Locke et al. | |
| 5,827,895 A | 10/1998 | Nutter et al. | |
| 6,096,350 A * | 8/2000 | Kemp et al. | 424/661 |
| 6,204,283 B1 | 3/2001 | Black et al. | |
| 6,646,014 B2 | 11/2003 | Watkins et al. | |
| 6,702,645 B2 | 3/2004 | Vanderpool | |
| 2001/0014346 A1* | 8/2001 | Watkins | 424/405 |
| 2002/0051804 A1 | 5/2002 | Probasco et al. | |
| 2003/0060379 A1 | 3/2003 | Souter et al. | |
| 2005/0043404 A1 | 2/2005 | Probasco et al. | |
| 2005/0049230 A1 | 3/2005 | Henrich et al. | |
| 2005/0220914 A1* | 10/2005 | Probasco et al. | 424/778 |
| 2006/0009122 A1 | 1/2006 | Swanson | |
| 2006/0013870 A1 | 1/2006 | Kuhrts | |
| 2007/0232188 A1 | 10/2007 | Probasco | |
| 2008/0026673 A1 | 1/2008 | Probasco | |

FOREIGN PATENT DOCUMENTS

GB 2330076 4/1999
JP 57080304 A * 5/1982

OTHER PUBLICATIONS

International Search Report for PCT/US07/23984.

(Continued)

*Primary Examiner*—Christopher R. Tate
*Assistant Examiner*—Deborah A. Davis
(74) *Attorney, Agent, or Firm*—Edwards Angell Palmer & Dodge LLP; Jeffrey D. Hsi, Esq.; Melissa Hunter-Ensor, Esq.

(57) ABSTRACT

As described below, the present invention provides methods and compositions for controlling a honey bee parasitic mite. In addition, the invention features compositions useful for the treatment or prevention of a parasitic mite infestation in a honey bee hive.

5 Claims, 5 Drawing Sheets

Hop Derivatives Efficacy Against Varroa Mites of Honey Bees

OTHER PUBLICATIONS

"Culpeper's Complete Herbal A book of Natural Remedies for Ancient Ills," Wordsworth Reference, pp. 134-135 (1995).

Jones, G., "Potential Control of Two-Spotted Spider Mite, *Tetranychus urticae Koch*, Using Hop β-Fraction," (1998) pp. 1-165, A thesis submitted for the degree of Doctor of Philosophy of the Univeristy of London and for the Diploma of Imperial College of Science, Technology & Medicine.

Jones et al., "Repellant and Oviposition-Deterring Effects of Hop-Beta Acids on the Two-Spotted Spider Mite *Tetranychus urticae*," Pesticide Science, vol. 47, No. 2, pp. 165-169 (1996).

Losel et al., The Potentional of Semidochemicals for Control of *Phorodon hummuli* (Homoptera: Aphididae), Pesticide Science, vol. 48, No. 4, pp. 293-303 (1996).

\* cited by examiner

Fig. 1 Hop Derivatives Efficacy Against Varroa Mites of Honey Bees

Fig. 2 Hop Erivatives Efficacy Against Varroa Mites of Honey Bees

Fig. 3 Hop Derivatives Efficacy Against Varroa Mites of Honey Bees

Fig. 4 Hop Derivatives Efficacy Against Varroa Mites of Honey Bees

Fig. 5 Hop Derivatives Efficacy Against Varroa Mites of Honey Bees

COMPOSITIONS AND METHODS FOR CONTROLLING A HONEY BEE PARASITIC MITE

BACKGROUND OF THE INVENTION

Honey bees, *Apis mellifera*, are required for the effective pollination of crops and are therefore critical to world agriculture. Honey bees also produce economically important products, including honey and bees wax. Honey bees are susceptible to a number of parasites and pathogens, including the ectoparasitic mite, *Varroa destructor*. *Varroa* mites parasitize pupae and adult bees and reproduce in the pupal brood cells. The mites use their mouths to puncture the exoskeleton and feed on the bee's hemolymph. These wound sites in the exoskeleton harbor bacterial infections, such as *Melissococcus pluton*, which causes European foulbrood. In addition, to their parasitic effects, *Varroa* mites are suspected to act as vectors for a number of honey bee pathogens, including deformed wing virus (DWV), Kashmir bee virus (KBV), acute bee paralysis virus (ABPV) and black queen cell virus (BQCV), and may weaken the immune systems of their hosts, leaving them vulnerable to infections. If left untreated *Varroa* infestations typically result in colony-level mortality. Maintaining a supply of strong honey bee colonies available for pollination is essential for the sustained production of farm crops worth more than $14 billion to U.S. agriculture. During the winter of 2004-2005, an estimated 40% of the honey bee colonies in the U.S. were weakened or collapsed due to *Varroa* infestation. Current methods of treating *Varroa* infestations are proving to be ineffective as the mites develop resistance to existing miticides. In addition, the use of such miticides may introduce injurious chemicals into honey that is intended for human consumption. New compositions and methods for treating or preventing *Varroa* mite infestations are urgently required. Desirably, such compositions would include only natural ingredients that pose no risk to human health.

SUMMARY OF THE INVENTION

As described below, the present invention features methods and compositions for controlling a honey bee parasitic mite or for the treatment or prevention of a parasitic mite infestation in a honey bee hive.

In general, the invention provides a method of controlling a honey bee parasitic mite (e.g., *Varroa* mite, tracheal mite). The method involves contacting the parasitic mite with an effective amount of a composition comprising a hop derivative (e.g., alpha acid, beta acid, or combination thereof), thereby controlling a honey bee parasitic mite. In one embodiment, the contacting of the mite occurs while the mite is in contact with a honey bee (e.g., honey bee egg, larva, or pupa).

In a related aspect, the invention provides a method of treating or preventing a parasitic mite infestation of a honey bee hive. The method involves contacting the hive with an effective amount of a composition comprising a hop derivative, thereby treating or preventing a parasitic mite infestation in a honey bee hive.

In another aspect, the invention provides a composition for treating or preventing a mite infestation, the composition comprising an effective amount of a hop derivative in a suitable form for delivery to a mite. Suitable forms include, for example, any one or more of a liquid, a powder, an oil, an emulsion, a paste, a capsule, a vapor, or any other form capable of delivering a hop derivative to a *Varroa* mite in contact with a honey bee or honey bee hive. If desired, the composition further comprises a carrier medium.

In yet another aspect, the invention provides a controlled release composition for treating or preventing a parasitic mite infestation, the composition comprising an effective amount of a hop derivative in a suitable form for delivery to a honey bee parasitic mite.

In yet another aspect, the invention provides a miticide delivery device, the device comprising a composition of any previous aspect. In one embodiment, the device is selected from the group consisting of a strip, controlled release strip, tablet, reservoir, polymer disc, evaporation device, fiber, tube, polymeric block, membrane, pellet, tray, and microcapillary. If desired, any of these devices can be formulated in a biodegradable form.

In yet another aspect, the invention provides a hive comprising a composition of any previous aspect.

In yet another aspect, the invention provides a honey bee product produced in a hive of any previous aspect. Honey bee products include, but are not limited to, honey, honey comb, and bees wax.

In yet another aspect, the invention provides a kit for the treatment or prevention of an parasitic mite infestation, the kit comprising an effective amount of a hop derivative in a form suitable for delivery to a site of infestation (e.g., a bee hive or a bee).

In yet another aspect, the invention provides a method of identifying a hop derivative that disrupts a biological function of a honey bee parasitic mite. The method involves contacting the parasitic mite with a test composition comprising a hop derivative; and assaying a parasitic mite biological function. In one embodiment, the test composition disrupts a parasitic mite biological function (e.g., kills or incapacitates the parasitic mite or reduces parasitic mite reproduction). In another embodiment, the method further includes the steps of contacting a honey bee with the test composition; and assaying a honey bee biological function. In yet another embodiment, the method identifies a test compound that does or does not disrupt a honey bee biological function. In another embodiment, the method identifies a test compound that kills a honey bee.

In a related aspect, the invention provides a method of identifying a hop derivative that does not disrupt a biological function of a honey bee. The method involves contacting the honey bee with a test composition comprising a hop derivative; and assaying a honey bee biological function. In one embodiment, the method identifies a test compound that does or does not disrupt a honey bee biological function. In another embodiment, the test compound kills a honey bee.

In various embodiments of any previous aspect, a hop derivative is an alpha acid or a beta acid. In other embodiments of a previous aspect, a composition of the invention contains an alpha acid, a beta acid, or a combination thereof, wherein the amount of alpha or beta acid in the composition ranges between 1% and 100%, where the bottom limit of the range is any integer between 1 and 99% and the upper limit of the range is any integer between 2% and 100%. Exemplary amounts of an alpha, a beta, or a combination thereof include at least 1%, 2.5%, 5%, 7.5%, 10%, 12%, 15%, 20%, 25%, 35%, 40%, 50%, 60%, 75%, 85%, 90% or 95% in a composition. In one particular embodiment, the composition comprises at least 1%, 2%, 2.5%, 3%, 5%, or 10% beta acid and at least 1%, 2%, 3%, 5%, 6%, 7.5%, 8%, 9%, 10%, 12%, or 15% alpha acids. In one embodiment of any of the above aspects, the contacting disrupts a biological function of a mite. Exemplary biological functions include any one or more of respiration, neural activity, locomotion, reproduction, or any other physiological activity required for mite survival. In one embodiment, the contacting kills the mite. In yet other embodiments, the composition of the invention is a controlled release composition wherein the hop derivative is released over the course of at least one week to 12 months. For example, the hop derivative is released over at least 5, 10, 14, 28, 36, 41, or 48 days; or is released over the course of 1, 2, 4, 6, 8, 10 or 12 weeks, or even for as long as 5, 6, 9, or 12 months.

Other features and advantages of the invention will be apparent from the detailed description, and from the claims.

DEFINITIONS

By "acarid" is meant an arachnid of the order Acarina, which includes mites and ticks.

By "alpha acid" is meant an organic acid derived from a hop plant (*Humulus lupulus*) having structural homology to a humulone, adhumulone, cohumulone, or an analog or derivative thereof. Humulone, adhumulone, and cohumulone are the three most abundant alpha acid analogs. Other exemplary derivatives of an alpha acid include, but are not limited to isoalpha acids, rhoisoalpha acids, tetrahydroisoalpha acids, and hexahydroisoalpha acids.

By "beta acid" is meant an organic acid derived from a hop plant (*Humulus lupulus*) having structural homology to a lupulone, adlupulone, colupulone or an analog or derivative thereof. Lupulone, adlupulone, and colupulone are the three most abundant beta acid analogs. Other exemplary derivatives of a beta acid include, but are not limited to, hulupones, hexahydrobeta acids and hexahydro hulupones.

By "biological function" is meant any physiological or behavioral activity of an organism. Exemplary biological functions include reproduction, respiration, neural activity, locomotion. Honey production is a biological function that is specific to a honey bee.

By "contacting" is meant touching, associating with, or having proximity to a composition. For example, a hop derivative may contact a hive either inside or outside of the hive structure.

By "controlled release" is meant released over the course of hours, days, weeks, or months.

By "controlling a parasitic mite" is meant inhibiting mite survival or reducing, slowing, or stabilizing the growth of a mite population.

By "comb" is meant sections of hexagonal bee wax cells that are used to rear honey bee progeny ("brood") and store honey and pollen.

By "effective amount of a miticide" is meant an amount effective to disrupt a mite biological function.

By "hive" is meant a structure that contains a bee colony. A modern box hive typically includes a bottom board, cover, and one or more boxes, stacked one above the other. Inside, each box contains a series of movable frames of comb or foundation held in a vertical position a bee space apart.

By "honey bee" is meant a Hymenopteran insect of the genus *Apis*. The term "honey bee" is not limited to the adult form of the insect, but encompasses all honey bee developmental stages, including but not limited to egg, larva, and pupa. Exemplary honey bee species include *Apis mellifera* and *Apis cerana*.

By "honey bee colony" is meant a community of bees. Honey bee colonies may occur in the wild or may be maintained by bee keepers.

By "honey bee parasitic mite" is meant any acarid that parasitizes a honey bee. Exemplary honey bee parasitic mites include *Varroa* mites and tracheal mites.

By "hop derivative" is meant any molecule that naturally occurs in hops (*Humulus lupulus*) and chemical derivatives thereof. Hop derivatives (e.g., alpha acids, beta acids) may be purified from hops or may be chemically synthesized.

By "infestation" is meant the colonization of a site or the parasitization of an organism by a pest.

By "miticide" is meant an agent that inhibits a biological function of a mite.

By "miticidal activity" is meant any activity that inhibits the growth, reproduction, or survival of a mite or other acarid.

By "preventing a mite infestation" is meant reducing the success that a mite infestation will be established in an *Apis* colony.

By "treating a mite infestation" is meant reducing, stabilizing, or slowing the growth of a mite population in an *Apis* colony.

DETAILED DESCRIPTION OF THE INVENTION

The present invention is directed to methods and compositions to control acarids and other related species of the family Varroidae. The invention is based, in part, on the discovery that naturally occurring components of hops are useful for the prevention or treatment of a *Varroa* mite infestation.

*Apis*

Honey bees are insects that pass through four life stages: the egg, larva, pupa and adult. Adult bees belong to one of three castes: queen, worker, or drone. The queen bee is the only female in the colony that is capable of reproduction and is responsible for all egg production. The worker bees are non-reproductive females who gather honey and care for the queen's progeny, or "brood." The drones are male bees that mate with the queen. The life cycle, from egg to adult bee, takes twenty-one days for worker bees and twenty-four days for drones. The queen bee lays each egg in a single cell of the comb. The egg generally hatches into a larva on the fourth day, which continues its development within the cell. On the ninth day the cell with the developing larva is capped with wax and the larva undergoes pupal metamorphosis. On day twenty-one, a new adult worker bee emerges.

Acarids

Acarids are small parasitic arachnids that act as parasites on a variety of plants and animals, including honey bees. Parasitic mites that prey on honey bees include *Varroa* mites (e.g., *Varroa destructor, Varroa jacobsoni*) and tracheal mites (e.g., *Acarapis woodi*) Tracheal mites are microscopic mites that inhabit the respiratory tubes of bees. *Varroa* mites are ectoparasites that feed on bee hemolymph, and infest wild and domestic honey bee colonies. *Varroa* mite reproduction begins when the adult female mite enters a brood cell shortly before it is capped. Drone brood, which is reared in larger cells than worker brood, is preferentially targeted for mite infestation. The female mite feeds on the larval hemolymph prior to depositing her eggs. The *Varroa* eggs eclose under the sealed cell, and the developing mites feed on the bee pupa. The first egg laid by the female *Varroa* develops into a male. Subsequent eggs develop into females that mate with their brother. The mated female mites along with their mother are released from the capped cell when the bee emerges. The female mites typically attach to adult bees between the abdominal segments or between body regions, where they feed on the bees' hemolymph. Adult bees serve as intermediate hosts and as a means of transport to new sites of infestation.

Desirably, miticides used in acarid control should address the following four needs: i) should disrupt a physiological function required for mite survival; ii) should cause no adult bee mortality; iii) should have no adverse effects on human bee keepers or honey intended for human consumption; and iv) should be capable of delivery into the hive.

Mite Control

Products used to control honey bee parasitic mite infestation reduce, stabilize, or slow the growth of a mite population in a hive or inhibit the growth, survival, reproduction, or other biological function of a honey bee parasitic mite. Methods for measuring parasitic mite infestation are known in the art. A number of parameters can be indicative of the level of infestation present in a bee colony: the number of mites present in a sample of bees from an infested hive can be used as one measure of the level of infestation present in the hive; bees reared in a hive having an active infestation are on average smaller than bees reared in a hive without infestation; thus, bee size or weight can be used as another measure of infestation; the amount of honey produced in an infected hive may be less than that produced in a healthy hive; accordingly, honey production could serve as yet another measure of the level of infestation; and finally, severe infestations result in complete loss of colonies. Thus, loss of colonies can be a measure of the level of infestation present in the hive. In one embodiment, a miticide of the invention reduces the level of infestation in a hive by at least 10%, 25%, 50%, 75% or even by 100%. In another embodiment, a miticide of the invention induces at least 50%, 60%, or 70% mite lethality. Preferably, the miticide induces 75%, 80%, 90%, or even 95% or 100% mite lethality. Screening methods are used to identify concentrations of hop derivatives that will be lethal to a mite (e.g., induce at least 70% mite lethality) while minimizing lethal effects on adult bees.

Alternatively, a miticide of the invention inhibits mite reproduction. Preferably, the miticide reduces mite reproduction by at least 25%, 50%, 75% or 100%. In another approach, the miticide disrupts a biological function required for acarid locomotion; such treatment allows the mite to be trapped, drowned, isolated, or otherwise removed from an area.

Miticide Screening

Commercial products that are currently being used to control mite infestation can be lethal to adult bees when administered at high concentrations, can have adverse effects on human bee keepers, and may contaminate honey intended for human consumption. Conventional miticides include Tau-Fluvalinate (a synthetic-pyrethroid compound used as a selective contact and stomach poison) and Coumaphos (a systemic organic phosphate) used on animals to control lice, ticks and mites. In contrast to conventional miticides, compositions of the invention contain safe natural products derived from hops. Hops have been used for centuries to flavor beer; thus, formulations comprising hop derivatives are generally safe. Miticidal compositions of the invention will not adversely affect human bee keepers or honey intended for human consumption.

Miticides of the invention contain concentrations of hop derivatives that have few or no adverse effects on honey bees during any of their life stages, but are effective in killing or disrupting the biological functioning of a mite. As reported herein, beta acids, a hop derivative, delivered at 4% concentration killed 87% of exposed mites after four hours while causing 0% lethality in adult bees. In one approach, mites are exposed to varying concentrations of hop derivatives to identify those concentrations that kill 50% to 100% of the exposed mite. Adult honey bees are then exposed to concentrations of hop derivatives having miticidal activity to identify those that have a minimal effect on honey bee survival. Preferably, at least 75%, 80%, 85%, 90%, 95%, or 100% of adult bees will survive following exposure to a miticidal composition. In a similar approach, the effect of hop derivatives on mite and honey bee reproduction is assessed. Screening assays are used to determine the concentration of a miticide that reduces the number of eggs laid by the female mite, reduces the number of eggs that hatch, or reduces the number of mites that grow to reproductive maturity; preferably, the reduction is by at least 25%, 50%, 75%, 85%, 95% or 100%.

Hop Derivatives

A hop derivative is a compound that occurs naturally in a hop plant (*Humulus lupulus*) or is chemically derived (either through natural biosynthetic processes (e.g., living organism metabolism (e.g., mammal, plant, bacteria)) or by synthetic processes using human intervention (e.g., chemical synthesis). Compositions of the invention include one or more compounds derived from hops. Of particular interest are the hop acids. Hops contain two major organic acid classes, alpha acids and beta acids. Hop acids are the bitter acid components of hops that are used in beer making. There are three major analogs for alpha acids, humulone, cohumulone, and adhumulone, and three major analogs for beta acids, lupulone, colupulone, and adlupulone. The percentages of the analogs present in the alpha acids and beta acids are variety-dependent. Thus, hop derivatives and hop products typically contain one or a mixture of these analogs. The percentage of analog present is dependent on the hop variety used to produce the derivative or product. Alpha acids and beta acids can be prepared by purification from natural hops and also by chemical synthesis according to traditional methods. Exemplary hop derivatives include beta acids, hexahydrobeta acids, rhoisoalpha acids, isoalpha acids, tetrahydroisoalpha acids, hexahydroisoalpha acids, magnesium salts of rhoisoalpha acids and magnesium salts of beta acids. Compositions comprising hop derivatives are also available commercially. John I. Haas, Inc. products containing hop derivatives include Betacide, Redihop®, Isohop®, Tetrahop Gold®, Hexahop Gold®, MgRIAA and MgBeta. The active ingredients in these products are beta acids, rhoisoalpha acids (RIAA), isoalpha acids (IAA), tetrahydroisoalpha acids (THIAA), hexahydroisoalpha acids (HHIAA), magnesium salts of rhoisoalpha acids (MgRIAA) and magnesium salts of beta acids MgBA), respectively. For convenience, the identities of these products are also listed in Table 1. These products and/or hop derivatives are typically diluted to a desired concentration for use in the methods of the invention.

Plant extracts are often used for the purification of compounds from plants (e.g., hops). An extract can be prepared by drying and subsequently cutting or grinding the dried material. The term "extract" refers to a concentrated preparation of the essential constituents of a plant, such as hops. Typically, an extract is prepared by drying and powderizing the plant. Optionally, the plant, the dried plant or the powderized plant may be boiled in solution. The extract may be used in liquid form, or it may be mixed with other liquid or solid herbal extracts. Alternatively, the extract may be obtained by further precipitating solid extracts from the liquid form. The extraction process may then be performed with the help of an appropriate choice of solvent, typically ethanol/water mixture, methanol, butanol, iso-butanol, acetone, hexane, petroleum ether or other organic solvents by means of maceration, percolation, repercolation, counter-current extraction, turbo-extraction, or by carbon-dioxide supercritical (temperature/pressure) extraction. The extract may then be further evaporated and thus concentrated to yield by means of air drying, spray drying, vacuum oven drying, fluid-bed drying or freeze-drying, the extract product.

Crude extracts are tested for miticidal activity as described herein. Further fractionation of a positive lead extract having miticidal activity is necessary to isolate chemical constituents responsible for the observed effect. Thus, the goal of the extraction, fractionation, and purification process is the careful characterization and identification of a chemical entity within the crude extract that disrupts a mite biological function. Methods of fractionation and purification of such heterogeneous extracts are known in the art. If desired, compounds shown to be useful as miticides are chemically modified according to methods known in the art.

Numerous methods are available for the chemical synthesis of candidate compounds. Such compounds can be synthesized from readily available starting materials using standard synthetic techniques and methodologies known to those of ordinary skill in the art. Synthetic chemistry transformations and protecting group methodologies (protection and deprotection) useful in synthesizing the compounds identified by the methods described herein are known in the art and include, for example, those such as described in R. Larock, Comprehensive Organic Transformations, VCH Publishers (1989); T. W. Greene and P. G. M. Wuts, Protective Groups in Organic Synthesis, 2nd ed., John Wiley and Sons (1991); L. Fieser and M. Fieser, Fieser and Fieser's Reagents for Organic Synthesis, John Wiley and Sons (1994); L. Paquette, ed., Encyclopedia of Reagents for Organic Synthesis, John Wiley and Sons (1995); and M. Verzele and D. De Keukeleire, Chemistry and Analysis of Hop and Beer Bitter Acids, Elsevier: Amsterdam (1991). Chemically synthesized alpha and beta acids can be separated from a reaction mixture and further purified by a method such as column chromatography, high pressure liquid chromatography, or recrystallization. As can be appreciated by the skilled artisan, further methods of synthesizing the compounds herein will be evident to those of ordinary skill in the art. Additionally, the various synthetic steps may be performed in an alternate sequence or order to give the desired compounds.

The compounds of this invention may contain one or more asymmetric centers and thus occur as racemates and racemic mixtures, single enantiomers, individual diastereomers and diastereomeric mixtures. All such isomeric forms of these compounds are expressly included in the present invention. The compounds of this invention may also be represented in multiple tautomeric forms, in such instances, the invention expressly includes all tautomeric forms of the compounds described herein (e.g., alkylation of a ring system may result in alkylation at multiple sites, the invention expressly includes all such reaction products). All such isomeric forms of such compounds are expressly included in the present invention. All crystal forms of the compounds described herein are expressly included in the present invention. As used herein, the compounds of this invention, including the compounds of formulae described herein, are defined to include derivatives. Derivatives include compounds of the invention that are modified by appending appropriate functionalities to enhance desired properties.

Acceptable salts of the compounds of this invention include those derived from acceptable inorganic and organic acids and bases. Examples of suitable acid salts include acetate, adipate, alginate, aspartate, benzoate, benzenesulfonate, bisulfate, butyrate, citrate, camphorate, camphorsulfonate, digluconate, dodecylsulfate, ethanesulfonate, formate, fumarate, glucoheptanoate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic acid, may be employed in the preparation of salts useful as intermediates in obtaining the compounds of the invention and their acceptable acid addition salts. Salts derived from appropriate bases include alkali metal (e.g., sodium), alkaline earth metal (e.g., magnesium), ammonium and N-(alkyl)$_4^+$ salts. This invention also envisions the quatemization of any basic nitrogen-containing groups of the compounds disclosed herein. Water or oil-soluble or dispersible products may be obtained by such quatemization.

Lower or higher doses than those recited herein may be required to effectively kill mites without adversely affecting honey bees. Specific dosage and treatment regimens are determined empirically as described herein. Compositions of the invention are also useful for preventing the establishment of an acarid infestation, for treating an established acarid infestation, and for maintaining the health of a hive previously treated for an acarid infestation.

Formulations

Hop derivatives can be provided to bees or bee hives in a number of convenient formulations. Formulations of the invention are used to target mites on the body of adult bees, in the brood cell, or in the hive. Desirably, the composition of the invention is active in the hive for at least forty-one days. This provides for the presence of the miticide for the entirety of the mite life cycle, which typically is completed over the course of twenty-one to thirty days. Where activity is maintained for a shorter period (e.g., seven, fourteen, twenty-one, or thirty days), repeated administration of a composition of the invention may be required. Compositions that are active for longer periods (e.g., two, three, six, nine, or twelve months) are also envisioned. Such compositions may be used for the long-term treatment or prevention of a mite infestation.

Powdered Formulations

Current miticides are introduced into the beehive on plastic non-biodegradable strips that are about 1" wide, 9" long and ¼" thick. Similar means could be used for the delivery of hop derivatives. In one embodiment, a composition comprising a hop derivative is provided in a powdered formulation. A substrate material is coated with a powdered formulation of hop acids, and the coating is subsequently encased in a layer of a substance that is attractive to bees, such as powdered sugar. This strip is placed inside the beehive where the adult bees chew into the powdered sugar and expose the powdered hop acids. The powdered hop acids get onto the body of the adult bees, thereby contacting mites present on the adult bees and causing them to die. Alternatively, the hop acids are consumed by the bees and enter their hemolymph, where they are subsequently consumed by the mites, thereby causing them to die.

Encapsulated Formulations

In one approach, a hop derivative is provided in an encapsulated formulation (liquid or powder). Preferably, a hop derivative in liquid or powder form is encapsulated in a coating that breaks down slowly inside the beehive. The coating provides for the long-term release of the hop derivative. Preferably, the composition is released over the course of two to six weeks (e.g., two, three, four, five, six weeks). Specific materials suitable for use in capsule materials include, but are not limited to, porous particulates or substrates such as silica, perlite, talc, clay, pyrophyllite, diatomaceous earth, gelatin and gels, polymers (e.g., polyurea, polyurethane, polyamide, polyester, etc.), polymeric particles, or cellulose. These include, for example, hollow fibers, hollow tubes or tubing which release a hop derivative or other compound specified above through the walls, capillary tubing which releases the compound out of an opening in the tubing, polymeric blocks of different shapes, e.g., strips, blocks, tablets, discs, which release the compound out of the polymer matrix, membrane systems which hold the compound within an impermeable container and release it through a measured permeable membrane, and combinations of the foregoing. Examples of such dispensing compositions are polymer laminates, polyvinyl chloride pellets, and microcapillaries. Encapsulation methods suitable for use in apiculture are described, for example, by Rieth et al., Journal of Apicultural Research 25(2):78-84 (1986).

Encapsulation processes are typically classified as chemical or mechanical. Examples of chemical processes for encapsulation include, but are not limited to, complex coacervation, polymer-polymer incompatibility, interfacial polymerization in liquid media, in situ polymerization, in-liquid drying, thermal and ionic gelation in liquid media, desolvation in liquid media, starch-based chemistry processes, trapping in cyclodextrins, and formation of liposomes. Examples of mechanical processes for encapsulation include, but are not limited to, spray drying, spray chilling, fluidized bed, electrostatic deposition, centrifugal extrusion, spinning disk or rotational suspension separation, annular-jet encapsulation, polymerization at liquid-gas or solid-gas interface, solvent evaporation, pressure extrusion or spraying into solvent extraction bath.

Microcapsules are also suitable for the long-term release of miticides. Microcapsules are small particles that contain a core material or active ingredient surrounded by a coating or shell. The size of the microcapsule typically varies from 1 to 1000 microns with capsules smaller than 1 micron classified as nanocapsules and capsules larger than 1000 microns as macrocapsules. Core payload usually varies from 0.1 to 98 weight percent. Microcapsules can have a variety of structures (continuous core/shell, multinuclear, or monolithic) and have irregular or geometric shapes.

In another approach, the hop derivative is provided in an oil-based delivery system. The oil-hop derivative mix is deposited on a solid substrate and the substrate containing the hop derivative is placed into the hive where it subsequently contacts and kills the mites. Oil release substrates include vegetable and/or mineral oils. In one embodiment, the substrate also contains a surface active agent that renders the composition readily dispersable in water; such agents include wetting agents, emulsifying agents, dispersing agents, and the like.

Miticides of the invention can also be provided as emulsions. Emulsion formulations can be found as water in oil (w/o) or oil in water (o/w). Droplet size can vary from the nanometer scale (colloidal dispersion) to several hundred microns. A variety of surfactants and thickeners are usually incorporated in the formulation to modify the size of the droplets, stabilize the emulsion, and modify the release.

Alternatively, miticides of the invention may also be formulated in a solid tablet and comprise (and preferably consist essentially of) an oil, a protein/carbohydrate material (preferably vegetable based), a sweetener and an active ingredient useful in the prevention or treatment of a parasitic infection in a honey bee. Methods for making such compositions are known in the art and are described, for example, in U.S. Patent Publication No. 20060008492.

In another approach, miticides of the invention are delivered in the form of a vapor. Methods for delivering such vapors to a hive are described, for example, in U.S. Patent Publication No. 20020151249.

Miticide Delivery

Devices for delivering pest control agents to bees or to a bee hive are known in the art. Such delivery devices include strips, controlled release strips, tablets, reservoirs, polymer discs, trays, and evaporation devices. If desired, the delivery device is provided in a biodegradable form. In particular, devices suitable for delivering a composition of the invention to a parasitic mite, to a honey bee, or to a honey bee hive are described, for example, in U.S. Patent Publication Nos. 20040229542, 20050090560, and 20020151249. Dispensing means and suitable compositions for controlled release are described in U.S. Pat. Nos. 6,843,985; 6,037,374; 5,750,129; 4,775,534; 5,849,317; 5,348,511; 6,037,374; 3,577,515, which are incorporated herein by reference in their entirety.

Kits

The invention provides kits for the treatment or prevention of an acarid infestation. In one embodiment, the kit includes a composition containing an effective amount of a hop derivative in a form suitable for delivery to a site of infestation (e.g., bee hive). In some embodiments, the kit comprises a container which contains a miticide; such containers can be boxes, ampules, bottles, vials, tubes, bags, pouches, blister-packs, or other suitable container forms known in the art. Such containers can be made of plastic, glass, laminated paper, metal foil, or other materials suitable for holding miticides.

If desired the miticide of the invention is provided together with instructions for administering it to a site of infestation. The instructions will generally include information about the use of the composition for the treatment or prevention of an acarid infestation. In other embodiments, the instructions include at least one of the following: description of the miticide; dosage schedule and administration for treatment or prevention of a miticide infestation; precautions; warnings; description of research studies; and/or references. The instructions may be printed directly on the container (when present), or as a label applied to the container, or as a separate sheet, pamphlet, card, or folder supplied in or with the container.

Examples

Hop Beta and Alpha Acids Used in Miticide Screening

Beta acids, alpha acids, and a combination of beta and alpha acids were screened for efficacy as miticides. Liquid test products containing beta acids were provided in a Beta-stab 10A® formulation (10% beta acids) hereinafter called "Betacide". Liquid test products containing alpha acids were provided in a Redihop® formulation (30% rhoisoalpha acids), Isohop® formulation (30% isoalpha acids), Tetrahop Gold® formulation (9% tetrahydroisoalpha acids), Hexahop Gold® formulation (5% hexahydroisoalpha acids and 5% tetrahydroisoalpha acids). A combination of alpha and beta acids were prepared by mixing equal parts Redihop® and Betacide. Powdered test products containing beta acids were provided by a magnesium salt formulation of beta acids. Powdered test products containing alpha acids were provided by magnesium salt formulations of Redihop®, Tetrahop Gold® and Hexahop Gold®.

Tests were carried out using the concentrations of beta, alpha, or beta and alpha acid combinations indicated in Table 1.

Specifically, in Tests 1-4: 5% beta acids as Betacide test solution, 15% rhoisoalpha acids as Redihop® test solution, and a 2.5% beta acids/7.5% rhoisoalpha acids combination was used.

In Tests 5-8, 4% beta acids as Betacide test solution, 30% rhoisoalpha acids concentration as Redihop® test solution, and a 2% beta acids/15% rhoisoalpha acids combination were used.

In Tests 9-12, 4% beta acids as Betacide test solution, 30% rhoisoalpha acids concentration as Redihop® test solution, and a 2% beta acids/15% rhoisoalpha acids combination were used.

In Tests 13-15, 30% isoalpha acids as Isohop®, 9% tetrahydroisoalpha acids as Tetrahop Gold®, and a combination of 5% tetrahydroisoalpha acids and 5% hexahydroisoalpha acids from Hexahop Gold® were used.

In Tests 16-19, 4.3% and 8.5% beta acids as a magnesium salt, and 65.5% rhoisoalpha acids as a magnesium salt of Redihop® were used.

In Tests 20-22, 25.3% tetrahydroisoalpha acids as a magnesium salt of Tetrahop Gold®, and a combination of 12.2% each of tetrahydroisoalpha acids and hexahydroisoalpha acids from magnesium salts of Hexahop Gold® were used.

Miticide Screening Assays

Tests using liquid hop products were conducted by absorbing one milliliter of test solution onto a filter paper in a Petri dish. Tests using the powdered hop products (magnesium salts) were conducted by spreading 0.5 gm of test powder evenly over filter paper in a Petri dish. Five to ten *Varroa* mites were then placed on the treated filter paper and mite survival was determined at one, four or five and twenty-four hours hour time points. Similar methods were used to evaluate the effect of the test compounds on adult honey bee survival. Adult honey bee survival was scored after twenty-two hours exposure to test product. Five to ten adult honey bees were placed in Petri dishes containing treated filter paper. Filter paper treated with water (for liquid test solutions) or cornstarch (for powdered test solutions) was used as a negative control for tests with the mites and the adult honey bees. All trials were replicated four times.

Table 1 outlines the tests and results of testing various hop products for miticidal activity.

TABLE 1

Hop Derivatives Efficacy Against Varroa Mites of Honey Bees

| Test Number | Figure Number | Product | Active Ingredient (ai) | Product Test acid % | | | | % Mortality/Exposure Time | | | |
|---|---|---|---|---|---|---|---|---|---|---|---|
| | | | | Conc. % | Alpha | Beta | Diluent | Mites | Hours | Bees | Hours |
| 1 | 1 | deionized water | none | NA | NA | NA | none | 7 | 4 | 0 | 22 |
| 2 | 1 | Betacide | beta acids | 10 | NA | 5 | deionized water | 73 | 4 | 20 | 22 |
| 3 | 1 | Redihop® | rhoisoalpha acids | 30 | 15 | NA | deionized water | 21 | 4 | 0 | 22 |
| 4 | 1 | Redihop® + Betacide as in test 1 + test 2 | | 30 + 10 | 7.5 | 2.5 | deionized water | 43 | 4 | 7 | 22 |
| 5 | 2 | deionized water | none | NA | NA | NA | none | 7 | 4 | 0 | 24 |
| 6 | 2 | Betacide | beta acids | 10 | NA | 4 | deionized water | 87 | 4 | 0 | 24 |
| 7 | 2 | Redihop® | rhoisoalpha acids | 30 | 30 | NA | deionized water | 68 | 4 | 0 | 24 |
| 8 | 2 | Redihop® + Betacide as in test 1 + test 2 | | 30 + 10 | 15 | 2 | deionized water | 80 | 4 | 0 | 24 |
| 9 | 3 | deionized water | none | NA | NA | NA | none | 0 | 1 | 0 | 24 |
| 10 | 3 | Betacide | beta acids | 10 | NA | 4 | deionized water | 20 | 1 | ND | 24 |
| 11 | 3 | Redihop® | rhoisoalpha acids | 30 | 30 | NA | deionized water | 13 | 1 | ND | 24 |
| 12 | 3 | Redihop® + Betacide as in test 1 + test 2 | | 30 + 10 | 15 | 2 | deionized water | 13 | 1 | ND | 24 |
| 13 | 3 | Isohop® | isoalpha acids | 30 | 30 | NA | deionized water | 70 | 1 | 33 | 24 |
| 14 | 3 | Tetrahop Gold® | tetrahydroisoalpha acids | 9 | 9 | NA | deionized water | 81 | 1 | 0 | 24 |
| 15 | 3 | Hexahop Gold® | hexahydroisoalpha acids plus tetrahydroisoalpha acids | 5 / 5 | 5 / 5 | NA / NA | deionized water | 100 | 1 | 7 | 24 |
| 16 | 4 | corn starch | none | NA | NA | NA | none | 13 | 5 | ND | ND |
| 17 | 4 | MgBeta | magnesium salt of beta acids | 59.5 | NA | 4.3 | corn starch | 38 | 5 | ND | ND |
| 18 | 4 | MgBeta | magnesium salt of beta acids | 59.5 | NA | 8.5 | corn starch | 67 | 5 | 0 | 24 |
| 19 | 4 | MgRIAA | magnesium salt of rhoisoalpha acids | 65.5 | 65.5 | NA | corn starch | 7 | 5 | ND | ND |
| 20 | 5 | corn starch | none | NA | NA | NA | none | 17 | 24 | 0 | 24 |
| 21 | 5 | MgTetrahop Gold | mg salt of tetrahydroisoalpha acids | 75.8 | 25.3 | NA | corn starch | 50 | 24 | 0 | 24 |
| 22 | 5 | MgHexahop Gold | mg salt of hexahydroisoalpha acids plus mg salt of tetrahydroisoalpha acids | 36.7 / 36.7 | 12.2 / 12.2 | NA / NA | corn starch | 50 | 24 | 0 | 24 |

Notes:
NA means Not Applicable,
ND means No Data

Results

Figure 1:
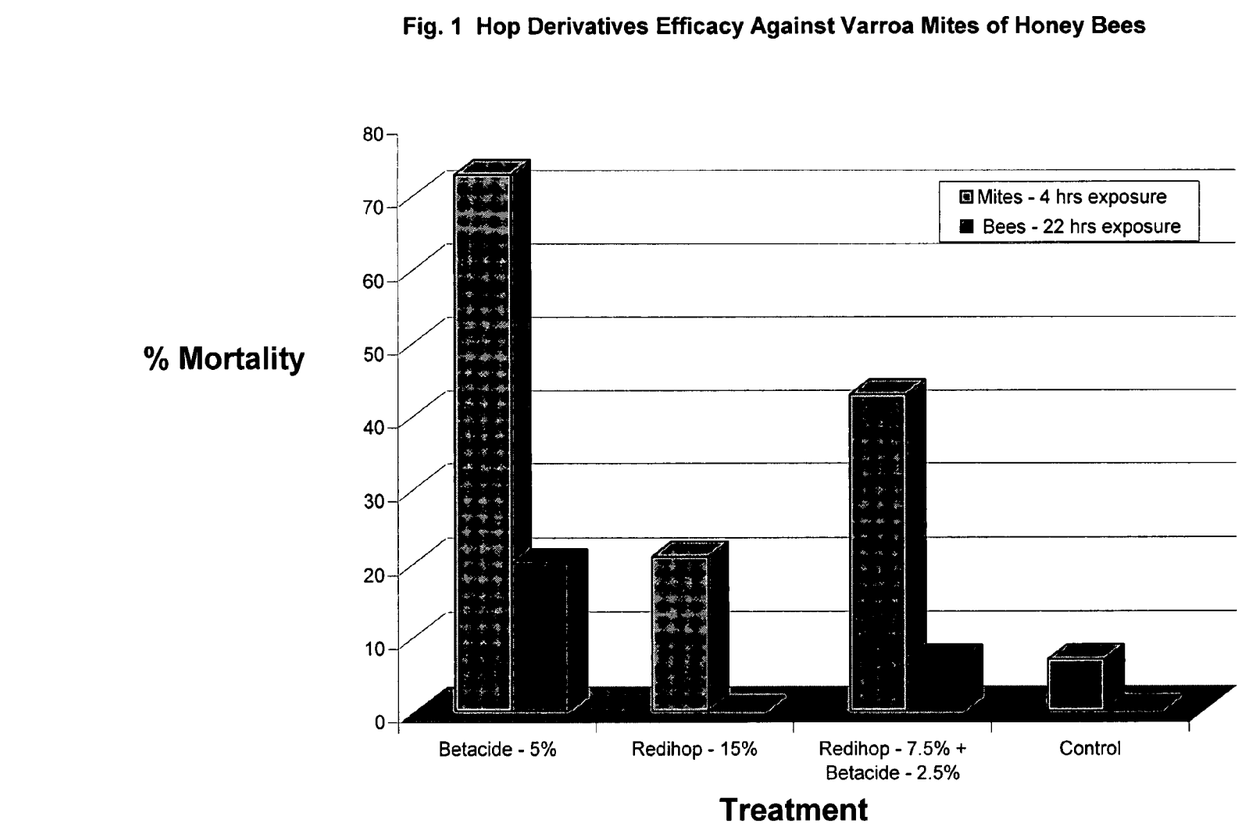
FIGS. 1-5 are graphs showing *Varroa* mite mortality and adult honey bee survival in response to hop product exposure.
Figure 2:
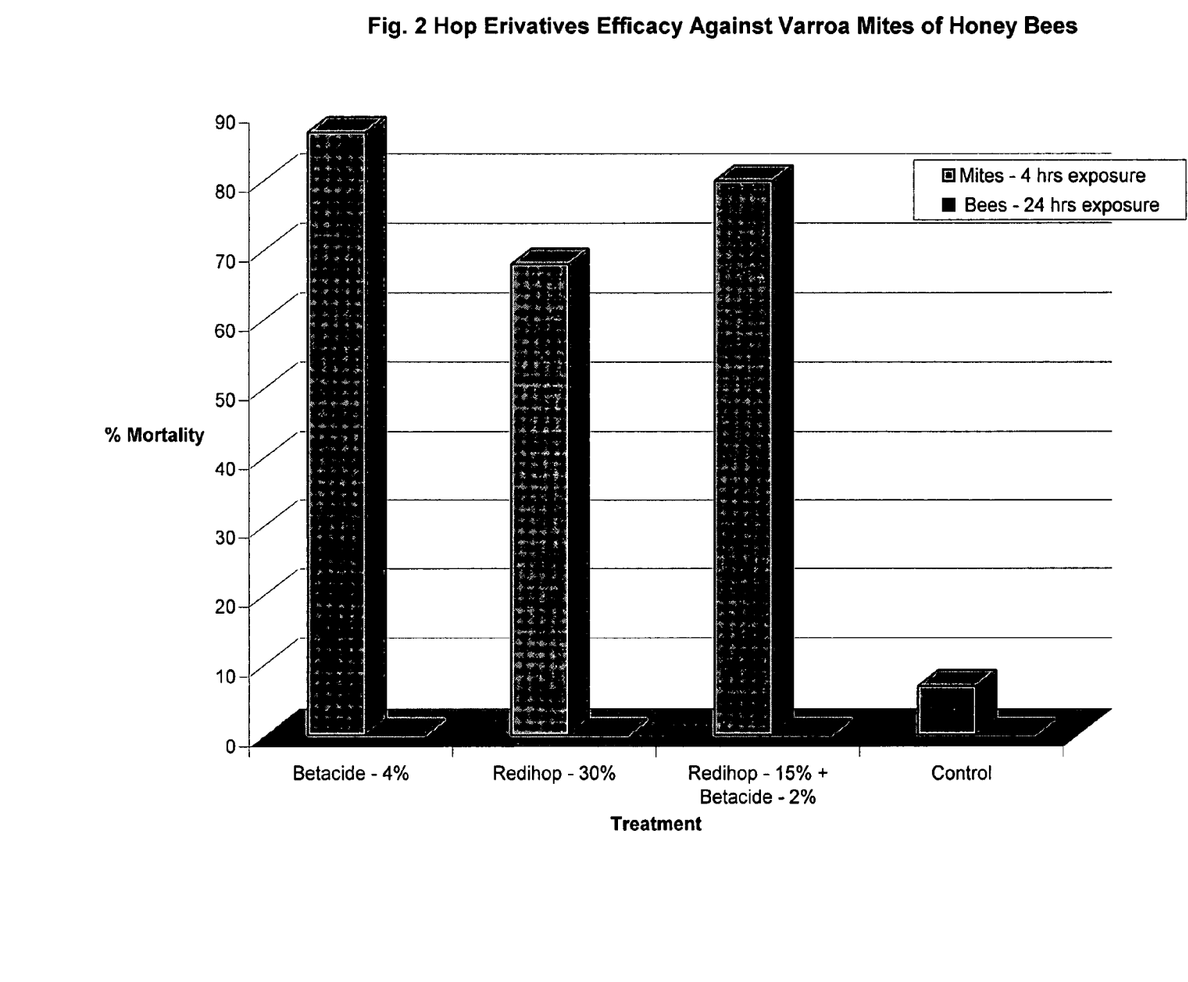
Figure 3:
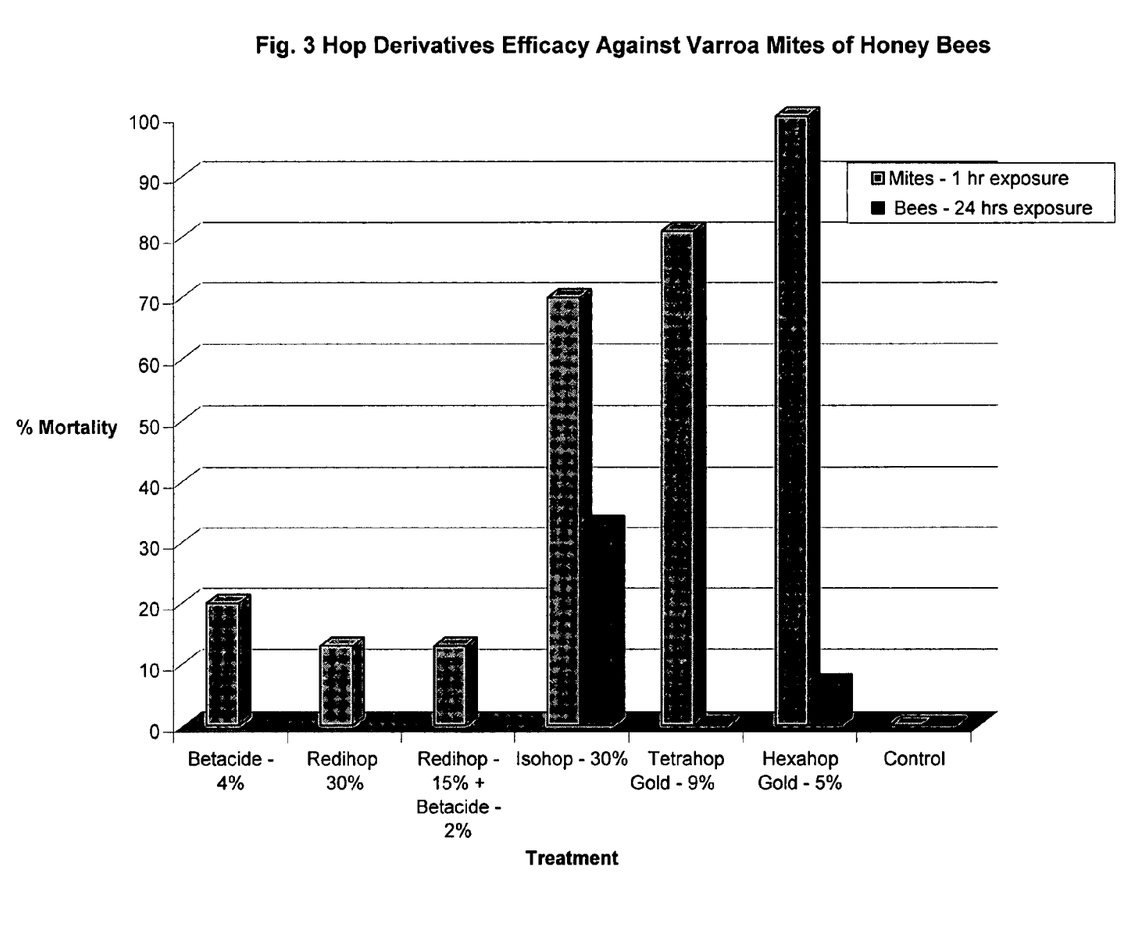
Figure 4:
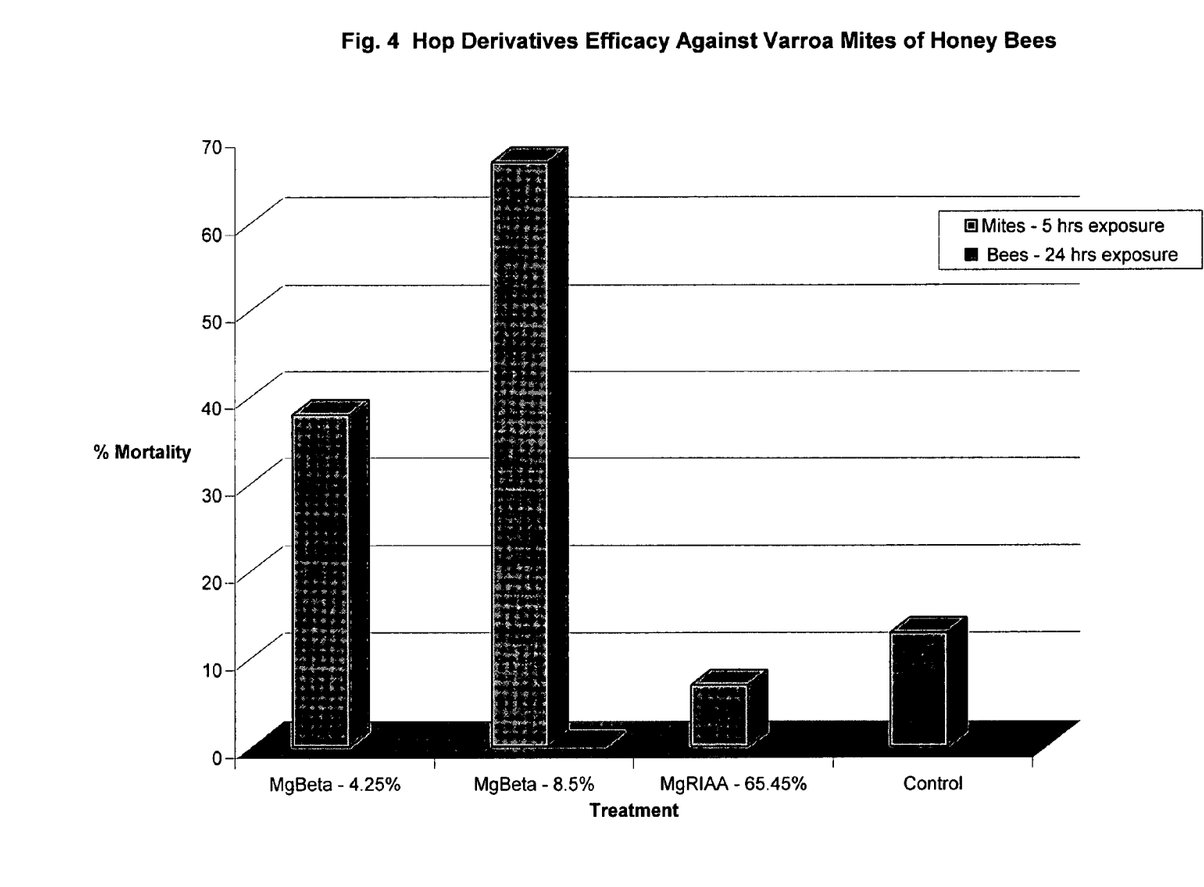
Figure 5:
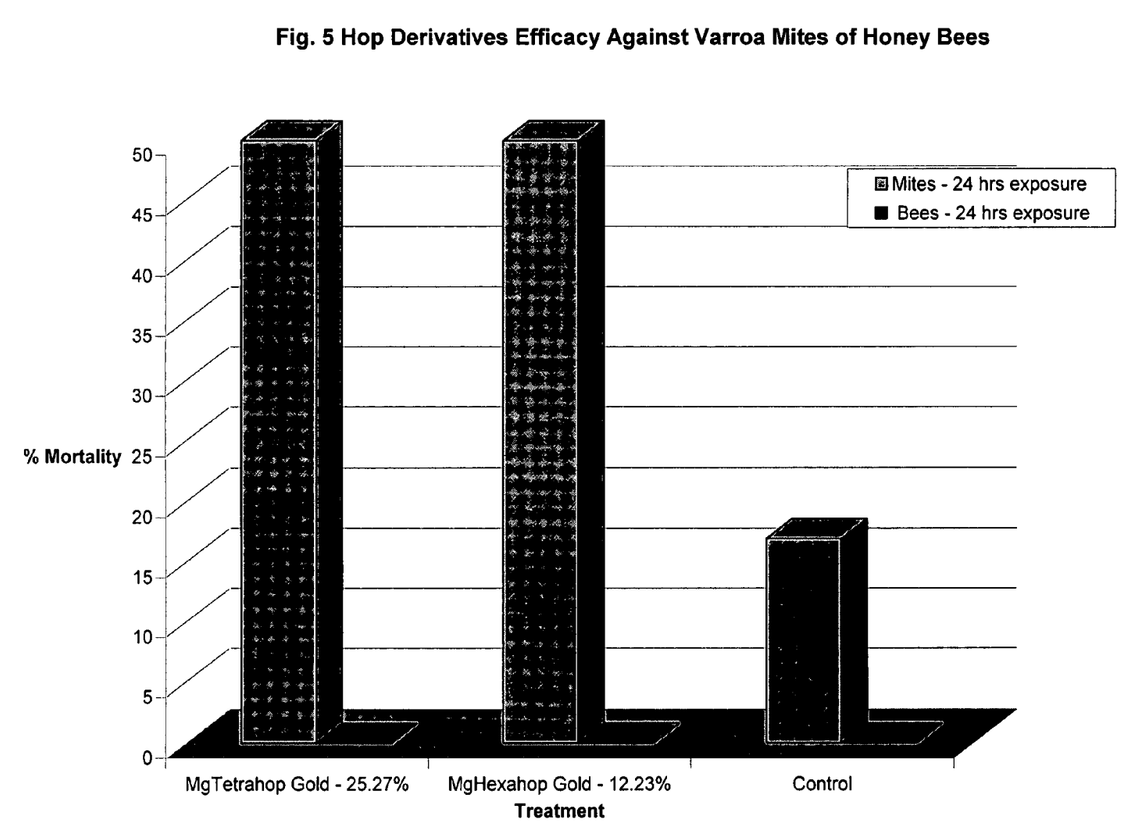

Results for the tests described in Table 1 are shown in FIGS. 1-5.

In Tests 1-4 after five hours exposure, 5% beta acids killed 73% of *Varroa* mites; 15% rhoisoalpha acids killed 21% of *Varroa* mites; and a combination of 2.5% beta acids/7.5% rhoisoalpha acids produced 43% mortality of mites. Under control conditions only 7% mite mortality was observed. The majority of adult bees survived exposure to these same concentrations of alpha and beta acids. Specifically, 100% adult bees survived exposure to rhoisoalpha acids; 80% of adult bees survived exposure to 5% beta acids; and 93% of adult bees survived exposure to the combination of 2.5% beta acids/7.5% alpha acids. These results are presented in Table 1 and FIG. 1.

In Tests 5-8 following four hours of exposure, 4% beta acids killed 87% of *Varroa* mites; 30% rhoisoalpha acids killed 68% of mites; and the combination of 15% rhoisoalpha acids and 2% beta acids killed 80% of mites. 7% mite mortality was observed under control conditions. Adult bees exposed to these same product concentrations for 24 hours showed 100% survival. These results are presented in Table 1 and FIG. 2.

In Tests 9-15 after one hour of exposure, 4% beta acids killed 20% of *Varroa* mites; 30% rhoisoalpha acids killed 13% of mites; the combination of 15% rhoisoalpha acids and 2% beta acids killed 13% of mites; 9% tetrahydroisoalpha acids killed 81% of mites; the combination of 5% tetrahydroisoalpha acids and 5% hexahydroisoalpha acids killed 100% of mites. No mite mortality was observed under control conditions. Adult bees exposed to these product concentrations for 24 hours showed 67% survival after exposure to isoalpha acids; 93% survival after exposure to the combination of 5% tetrahydroisoalpha acids and 5% hexahydroisoalpha acids; 100% survival after exposure to 9% tetrahydroisoalpha acids; and 100% survival after exposure to control conditions. These results are presented in Table 1 and FIG. 3.

In Tests 16-19, after five hours of exposure, 8.5% beta acids in the form of a magnesium salt killed 67% of *Varroa* mites; 65.45% rhoisoalpha acids in the form of a magnesium salt killed 7% of *Varroa* mites. 13% of mites died under control conditions. 100% of bees survived after 24 hours exposure to 8.5% beta acids as a magnesium salt. These results are presented in Table 1 and FIG. 4.

In Tests 20-22 after 24 hours of exposure, 25.27% tetrahydroisoalpha acids in the form of the magnesium salt killed 50% of *Varroa* mites; and a combination of 12.23% tetrahydroisoalpha acids and 12.23% hexahydroisoalpha acids both in the form of magnesium salt killed 50% kill of *Varroa* mites. 17% kill of mites died under control conditions. 100% of adult honey bees survived for 24 hours under the same conditions. These results are presented in Table 1 and FIG. 5.

OTHER EMBODIMENTS

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or sub combination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A box hive comprising an effective amount of a miticide selected from the group consisting of alpha acids, beta acids, or a combination of alpha and beta acids, wherein the alpha and beta acids are purified or extracted from hops, and wherein the miticide is sufficient to disrupt a honey bee parasitic mite biological function.

2. The hive of claim 1, wherein the miticide comprises at least about 1%, 5%, or 10% alpha acids.

3. The hive of claim 1, wherein the miticide comprises at least about 1%, 5%, or 10% beta acids.

4. The hive of claim 1, wherein the miticide comprises at least about 1% alpha and at least about 1% beta acids.

5. The hive of claim 1, wherein the amount of alpha and/or beta acids is sufficient to kill a mite.

* * * * *